(12) United States Patent
Fallon et al.

(10) Patent No.: US 8,720,913 B2
(45) Date of Patent: May 13, 2014

(54) PORTABLE PERITONEAL DIALYSIS CARTS AND RELATED SYSTEMS

(75) Inventors: Joseph Michael Fallon, Dixon, CA (US); Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 280 days.

(21) Appl. No.: 12/850,237

(22) Filed: Aug. 4, 2010

(65) Prior Publication Data

US 2011/0040242 A1 Feb. 17, 2011

Related U.S. Application Data

(60) Provisional application No. 61/232,931, filed on Aug. 11, 2009.

(51) Int. Cl.
*B62B 3/04* (2006.01)

(52) U.S. Cl.
USPC ............ 280/47.35; 280/651; 280/79.11; 280/79.2

(58) Field of Classification Search
USPC ............ 280/35, 47.34–47.371, 651, 641, 280/79.11–79.3, 42, 47.18, 47.2, 47.27
See application file for complete search history.

(56) References Cited

U.S. PATENT DOCUMENTS

| | | |
|---|---|---|
| 3,927,955 A | 12/1975 | Spinosa et al. |
| 3,985,135 A | 10/1976 | Carpenter et al. |
| 4,026,669 A | 5/1977 | Leonard et al. |
| 4,303,376 A | 12/1981 | Siekmann |
| 4,370,983 A | 2/1983 | Lichtenstein |
| 4,382,753 A | 5/1983 | Archibald |
| 4,436,620 A | 3/1984 | Bellotti et al. |
| 4,453,932 A | 6/1984 | Pastrone |
| 4,479,762 A | 10/1984 | Bilstad et al. |
| 4,486,189 A | 12/1984 | Troutner et al. |
| 4,623,328 A | 11/1986 | Hartranft |
| 4,628,499 A | 12/1986 | Hammett |
| 4,643,713 A | 2/1987 | Viitala |
| 4,644,876 A * | 2/1987 | Thomas ............... 108/192 |
| 4,657,490 A | 4/1987 | Abbott |
| 4,662,906 A | 5/1987 | Matkovich et al. |

(Continued)

FOREIGN PATENT DOCUMENTS

| | | |
|---|---|---|
| DE | 198 37 667 | 3/2000 |
| DE | 100 42 324 | 2/2002 |

(Continued)

OTHER PUBLICATIONS

Acumen, "Acute Dialysis Machine Brief Operating Instructions," Software Version 1.0, pp. 1-146.

(Continued)

*Primary Examiner* — Jeffrey J Restifo
*Assistant Examiner* — Erez Gurari
(74) *Attorney, Agent, or Firm* — Fish & Richardson P.C.

(57) ABSTRACT

A lightweight, easy-to-assemble, and portable cart for the performance of peritoneal dialysis is disclosed. The cart includes a top shelf, bottom shelf, and at least four adjustable connecting members or legs. The top shelf has a top surface designed to receive a PD cycler, and at least one hook to hang bags of solution. Various components of the cart include a plastic and foaming agent additive.

19 Claims, 7 Drawing Sheets

(56) References Cited

U.S. PATENT DOCUMENTS

| | | |
|---|---|---|
| 4,666,598 A | 5/1987 | Heath et al. |
| 4,676,467 A | 6/1987 | Palsulich |
| 4,710,166 A | 12/1987 | Thompson et al. |
| 4,716,520 A | 12/1987 | Locke et al. |
| 4,778,451 A | 10/1988 | Kamen |
| 4,798,090 A | 1/1989 | Heath et al. |
| 4,808,161 A | 2/1989 | Kamen |
| 4,826,482 A | 5/1989 | Kamen |
| 4,828,543 A | 5/1989 | Weiss et al. |
| 4,840,542 A | 6/1989 | Abbott |
| 4,902,282 A | 2/1990 | Bellotti et al. |
| 4,927,411 A | 5/1990 | Pastrone et al. |
| 4,950,134 A | 8/1990 | Bailey et al. |
| 4,976,162 A | 12/1990 | Kamen |
| 4,997,464 A | 3/1991 | Kopf |
| 5,002,471 A | 3/1991 | Perlov |
| 5,036,886 A | 8/1991 | Olsen et al. |
| 5,061,236 A | 10/1991 | Sutherland et al. |
| 5,088,515 A | 2/1992 | Kamen |
| 5,098,262 A | 3/1992 | Wecker et al. |
| 5,100,380 A | 3/1992 | Epstein et al. |
| 5,100,699 A | 3/1992 | Roeser |
| 5,116,021 A | 5/1992 | Faust et al. |
| 5,116,316 A | 5/1992 | Sertic et al. |
| 5,146,713 A | 9/1992 | Grafius |
| 5,151,019 A | 9/1992 | Danby et al. |
| 5,167,837 A | 12/1992 | Snodgrass et al. |
| 5,171,029 A | 12/1992 | Maxwell et al. |
| 5,178,182 A | 1/1993 | Kamen |
| 5,187,990 A | 2/1993 | Magussen et al. |
| 5,193,990 A | 3/1993 | Kamen et al. |
| 5,211,201 A | 5/1993 | Kamen et al. |
| 5,241,985 A | 9/1993 | Faust et al. |
| 5,247,434 A | 9/1993 | Peterson et al. |
| 5,250,027 A | 10/1993 | Lewis et al. |
| 5,252,044 A | 10/1993 | Raines et al. |
| 5,279,556 A | 1/1994 | Goi et al. |
| 5,302,093 A | 4/1994 | Owens et al. |
| 5,311,908 A | 5/1994 | Barone et al. |
| 5,315,632 A | 5/1994 | Flynn et al. |
| 5,317,044 A * | 5/1994 | Mooney et al. ................. 521/78 |
| 5,324,422 A | 6/1994 | Colleran et al. |
| 5,330,425 A | 7/1994 | Utterberg |
| 5,350,357 A | 9/1994 | Kamen et al. |
| D351,470 S | 10/1994 | Scherer et al. |
| 5,353,837 A | 10/1994 | Faust |
| 5,395,351 A | 3/1995 | Munsch |
| 5,421,208 A | 6/1995 | Packard et al. |
| 5,421,823 A | 6/1995 | Kamen et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,634 A | 7/1995 | Brown |
| 5,438,510 A | 8/1995 | Bryant et al. |
| 5,441,636 A | 8/1995 | Chevallet et al. |
| 5,445,506 A | 8/1995 | Afflerbaugh et al. |
| 5,447,286 A | 9/1995 | Kamen et al. |
| 5,450,743 A | 9/1995 | Buote |
| 5,462,416 A | 10/1995 | Dennehey et al. |
| 5,462,417 A | 10/1995 | Chapman |
| 5,474,683 A | 12/1995 | Bryant et al. |
| 5,478,211 A | 12/1995 | Dominiak et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,514,069 A | 5/1996 | Brown et al. |
| 5,514,102 A | 5/1996 | Winterer et al. |
| 5,538,405 A | 7/1996 | Patno et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,013 A | 9/1996 | Owens et al. |
| 5,570,716 A | 11/1996 | Kamen et al. |
| 5,578,070 A | 11/1996 | Utterberg |
| 5,609,572 A | 3/1997 | Lang |
| 5,614,677 A | 3/1997 | Wamsiedler et al. |
| 5,628,908 A | 5/1997 | Kamen et al. |
| 5,630,710 A | 5/1997 | Tune et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,658,133 A | 8/1997 | Anderson et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,741,125 A | 4/1998 | Neftel et al. |
| 5,746,708 A | 5/1998 | Giesler et al. |
| 5,755,683 A | 5/1998 | Houle et al. |
| 5,764,034 A | 6/1998 | Bowman et al. |
| 5,771,914 A | 6/1998 | Ling et al. |
| 5,772,635 A | 6/1998 | Dastur et al. |
| 5,772,637 A | 6/1998 | Heinzmann et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,887,878 A * | 3/1999 | Tisbo et al. ................. 280/47.19 |
| 5,906,598 A | 5/1999 | Giesler et al. |
| 5,935,099 A | 8/1999 | Peterson et al. |
| 5,938,634 A | 8/1999 | Packard |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,065,941 A | 5/2000 | Gray et al. |
| 6,068,612 A | 5/2000 | Bowman et al. |
| 6,074,359 A | 6/2000 | Keshaviah et al. |
| 6,099,492 A | 8/2000 | Le Boeuf |
| 6,118,207 A | 9/2000 | Ormerod et al. |
| 6,129,517 A | 10/2000 | Danby et al. |
| 6,136,565 A | 10/2000 | Best et al. |
| 6,154,605 A | 11/2000 | Aonuma |
| 6,164,621 A | 12/2000 | Bouchard et al. |
| 6,165,154 A | 12/2000 | Gray et al. |
| 6,179,801 B1 | 1/2001 | Holmes et al. |
| 6,184,356 B1 | 2/2001 | Anderson et al. |
| 6,196,987 B1 | 3/2001 | Holmes et al. |
| 6,200,287 B1 | 3/2001 | Keller et al. |
| 6,208,107 B1 | 3/2001 | Maske et al. |
| 6,220,295 B1 | 4/2001 | Bouchard et al. |
| 6,223,130 B1 | 4/2001 | Gray et al. |
| 6,227,807 B1 | 5/2001 | Chase |
| 6,228,047 B1 | 5/2001 | Dadson |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,316,864 B1 | 11/2001 | Ormerod |
| 6,322,488 B1 | 11/2001 | Westberg et al. |
| 6,325,775 B1 | 12/2001 | Thom et al. |

(56) References Cited

U.S. PATENT DOCUMENTS

| | | |
|---|---|---|
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,489,896 B1 | 12/2002 | Platt et al. |
| 6,491,656 B1 | 12/2002 | Morris |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,969,373 B2 | 11/2005 | Schwartz et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,267,661 B2 | 9/2007 | Susi |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,789,849 B2 | 9/2010 | Busby et al. |
| 7,815,595 B2 | 10/2010 | Busby et al. |
| 2001/0034502 A1 | 10/2001 | Moberg |
| 2001/0037763 A1 | 11/2001 | Deguchi et al. |
| 2002/0045851 A1 | 4/2002 | Suzuki et al. |
| 2002/0062105 A1 | 5/2002 | Tanner et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman, Jr. et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0051265 A1* | 3/2004 | Nadeau ............... 280/47.35 |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |

(56) References Cited

U.S. PATENT DOCUMENTS

| | | |
|---|---|---|
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0001380 A1* | 1/2005 | Winter et al. ............. 273/309 |
| 2005/0023786 A1* | 2/2005 | Delmerico ............. 280/79.11 |
| 2005/0054968 A1 | 3/2005 | Giannella |
| 2005/0165354 A1 | 7/2005 | Schwartz et al. |
| 2005/0209563 A1 | 9/2005 | Hopping et al. |
| 2005/0230292 A1 | 10/2005 | Beden et al. |
| 2006/0079826 A1 | 4/2006 | Beden et al. |
| 2006/0195064 A1 | 8/2006 | Plahey et al. |
| 2007/0112297 A1* | 5/2007 | Plahey et al. ............. 604/28 |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0208103 A1 | 8/2008 | Demers et al. |
| 2009/0004033 A1 | 1/2009 | Demers et al. |
| 2011/0185722 A1 | 8/2011 | Sebesta et al. |

FOREIGN PATENT DOCUMENTS

| | | |
|---|---|---|
| DE | 100 46 651 | 4/2002 |
| DE | 100 53 441 | 5/2002 |
| DE | 101 57 924 | 5/2002 |
| DE | 101 43 137 | 4/2003 |
| EP | 0728509 | 8/1996 |
| EP | 0856321 | 8/1998 |
| EP | 0 947 814 B2 | 10/1999 |
| EP | 0 956 876 A1 | 11/1999 |
| EP | 1529545 | 5/2005 |
| JP | 04-191755 | 7/1992 |
| JP | 06-002650 | 1/1994 |
| JP | 06-154314 | 6/1994 |
| JP | 11-347115 | 12/1999 |
| JP | 2000-070358 | 3/2000 |
| WO | WO 84/02473 | 7/1984 |
| WO | WO 86/01115 | 2/1986 |
| WO | WO 97/16214 | 5/1997 |
| WO | WO 97/37703 | 10/1997 |
| WO | WO 98/22165 | 5/1998 |
| WO | WO 00/23140 | 4/2000 |
| WO | WO 00/33898 | 6/2000 |
| WO | WO 01/17605 | 3/2001 |
| WO | WO 02/25225 | 3/2002 |
| WO | WO2011091975 A1 | 8/2011 |

OTHER PUBLICATIONS

Gambro®, "Prismaflex™ anticipating critical care needs and taking our innovative response . . . to new heights," © 2004, Gambro Inc., Lakewood, CO, 8 pp.

Gambro®, "DEHP-free cartridge blood sets," © Nov. 2004, Gambro, Inc., Lakewood, CO, 4 pp.

Sleep Safe™ Operating Instructions, Software Version 0.9, Part No. 677 805 1, Fresenius Medical Care, Aug. 2000.

Gambro®, Prisma® HF 1000, "For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Liberty Cycler User's Guide©, 2008, pp. 1-174.

Manns, Markus et al., "The acu-men: A new device for continuous renal replacement therapy in acute renal failure," Kidney International, vol. 54, pp. 268-274, 1998.

Newton IQ Cycler Operator Manual, Part No. 470203 Rev. F, 2000-2006.

Operator's Instructions, Fresenius 90/2 Peritoneal Therapy Cycler, Part No. 470016 Rev. B, 1991.

Operator's Manual, Serena, Program Version 3.xx—English.

Sleep Safe Technical Manual, Part No. 677 807 1.

Glenn Avolio, "Principles of Rotary Optical Encoders," Sensors Journal of Machine Perception, vol. 10, No. 4, pp. 10-18, 1993.

* cited by examiner

PORTABLE PERITONEAL DIALYSIS CARTS AND RELATED SYSTEMS

CROSS-REFERENCE TO RELATED APPLICATIONS

This application claims the benefit of U.S. Application Ser. No. 61/232,931, filed on Aug. 11, 2009, which is incorporated by reference herein.

TECHNICAL FIELD

The present invention relates peritoneal dialysis carts and related systems.

BACKGROUND

Dialysis to support a patient whose renal function has decreased to the point where the kidneys can no longer sufficiently function is well known. Generally, two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because the treatment is extracorporeal, it requires special machinery and generally, a visit to a center or hospital that performs the treatment.

Peritoneal dialysis (hereafter "PD") was developed to provide an alternative therapy to hemodialysis. PD utilizes the patient's own peritoneum (a membranous lining of the abdominal cavity) as a semi-permeable membrane. With its good perfusion, the peritoneum is capable of acting as a natural semi-permeable membrane.

PD periodically infuses sterile aqueous solution into the peritoneal cavity. This aqueous solution is called PD solution or dialysate. Diffusion and osmosis exchanges take place between the solution and the blood stream across the peritoneum. These exchanges remove the waste products that the kidneys normally excrete. The waste products typically consist of solutes like urea and creatinine. The kidneys also function to maintain proper levels of other substances, such as sodium and water, which also need to be regulated by dialysis. The diffusion of water and solutes across the peritoneal membrane during dialysis is called ultrafiltration.

In continuous ambulatory PD, a dialysis solution is introduced into the peritoneal cavity utilizing a catheter, normally placed by a doctor. An exchange of solutes between the dialysate and the blood is achieved by diffusion.

Certain PD machines are automated. These machines are called cyclers. Cyclers are generally designed to automatically infuse, dwell, and drain PD solution to and from the patient's peritoneal cavity. A cycler is particularly attractive to a PD patient because it can be used at night while the patient is asleep. This frees the patient from the day-to-day demands of continuous ambulatory PD during his/her waking and working hours.

The treatment typically lasts for several hours. It often begins with an initial drain cycle to empty the peritoneal cavity of spent dialysate. The sequence then proceeds through a succession of fill, dwell, and drain phases that follow one after the other. Each phase is called a cycle.

Unlike hemodialysis machines, which are typically operated by doctors or trained technicians, PD machines may be operated by the patient. Many PD patients travel which require those patients to take their PD apparatus with them in a car, train, or plane.

SUMMARY

In general, the invention relates to portable peritoneal dialysis carts and related systems.

In some aspects of the invention, a cart includes a top shelf, a bottom shelf, and at least four connecting members which attach to the top and bottom shelves.

The top shelf has a top surface designed for a cycler to sit on top. The top shelf may include indentations that correspond with the feet or bottom surface of the cycler, so that the cycler cannot easily slip off of the surface of the top shelf. The top shelf may additionally comprise one or more tapered hooks or fingers for loading and hanging dialysis solution bags therefrom. The hooks may hold and support bags that hold between approximately 1 liter and 6 liters of solution.

In some embodiments, at least four connecting members connect to the bottom surface of the top shelf and the top surface of the bottom shelf. The connecting members are approximately parallel to each other, and the top shelf is approximately parallel to the bottom shelf. The connecting members may be adjustable so that the height of the top shelf may be raised or lowered to optimize treatment for the patient.

Wheels or casters may be connected to the bottom surface of the bottom shelf so that the cart may be easily wheeled on a variety of floor surfaces.

In certain embodiments, the shelves and connecting members are manufactured by injection molding of plastic with a foaming agent additive. This method reduces the cost of manufacturing significantly and allows that cost-savings to be passed along to the patient. Furthermore, the cart and its components made of injection-molded plastic with a foaming agent additive are significantly more lightweight than many counterparts made by standard injection molding. However, the cart remains sturdy and able to withstand the weight of the cycler and solution bags without undue stress or loss of balance.

The cart is easy to assemble and disassemble, and may be assembled and disassembled without any tools. Color in the plastic and foaming agent eliminates the need for painting the cart, thereby increasing the sterility and cost savings of the cart. Furthermore, the fully-assembled cart weighs less than approximately 20 pounds.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
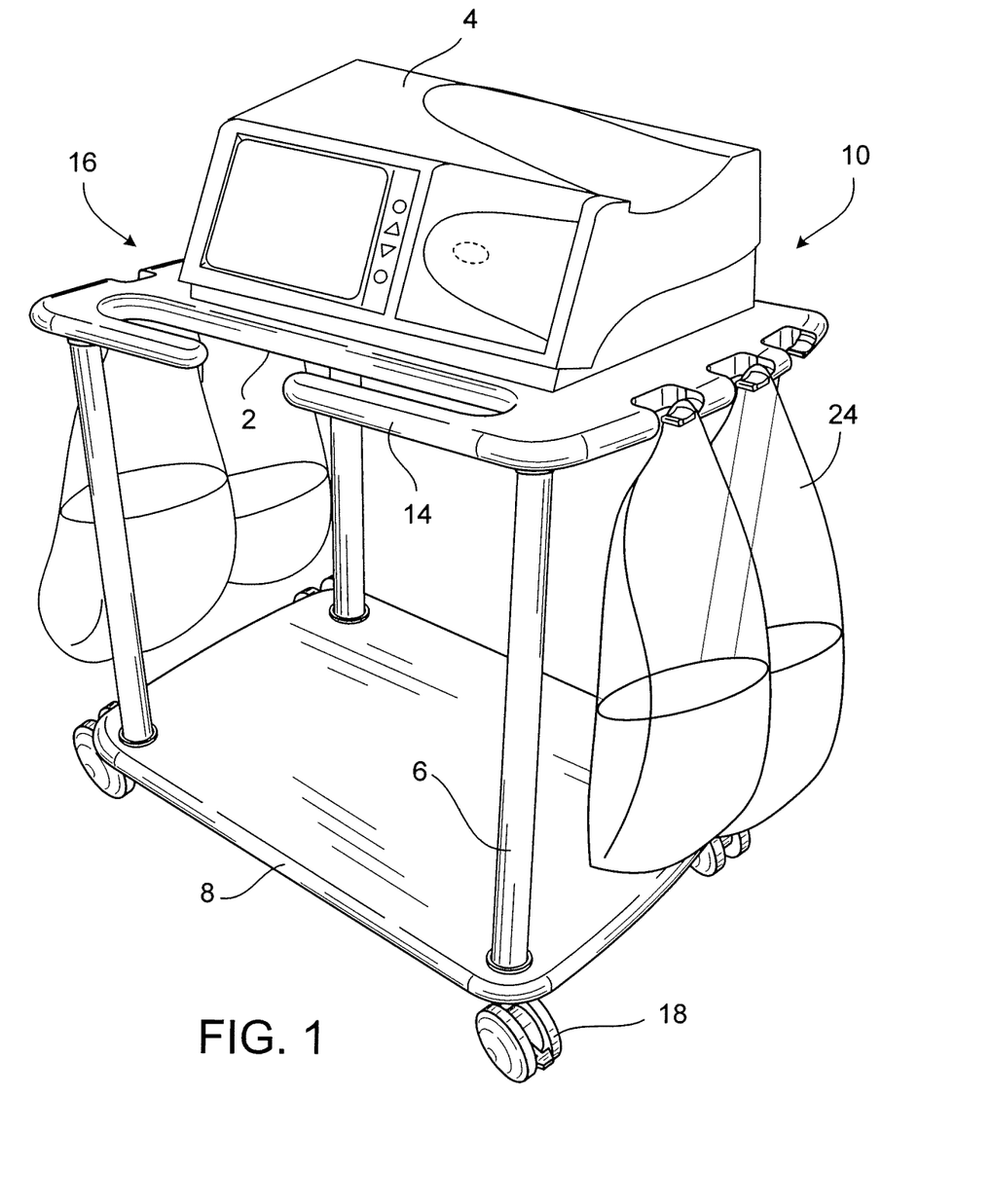
FIG. 1 is a perspective view of an apparatus and portable cart for performing peritoneal dialysis.
Figure 2:
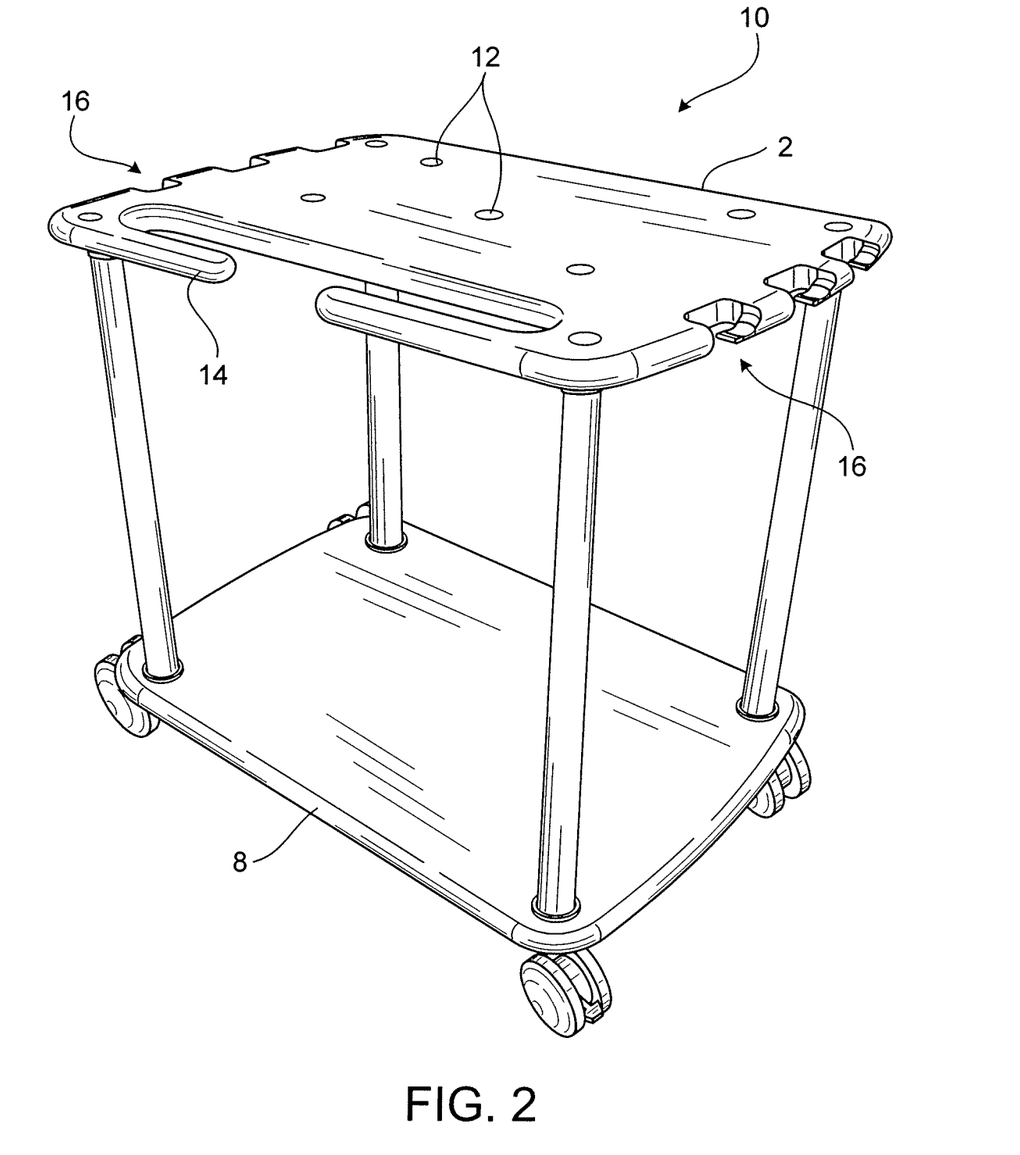
FIG. 2 is a perspective view of the portable cart of FIG. 1.

Referring to FIGS. 1 and 2, a portable PD cart 10 includes a top shelf 2 that has a top surface designed to accommodate seating a PD cycler 4. The top shelf 2 may include one or more indentations 12 that correspond with the feet or bottom surface of the cycler 4. The one or more indentations 12 secure the cycler 4 to the top shelf 2 so that the cycler 4 does not slip around on, or off of, the surface of the top shelf 2 as the cart 10 is rolled along a floor surface. Other non-slip materials may be adhered to or included in the top surface of the top shelf 2 to accomplish the same goal. For example, non-slip tracking may be laid down on the top surface, the top surface may further comprise a course material that inhibits slipping, or guard rails may line the edges of the top surface.

Figure 3:
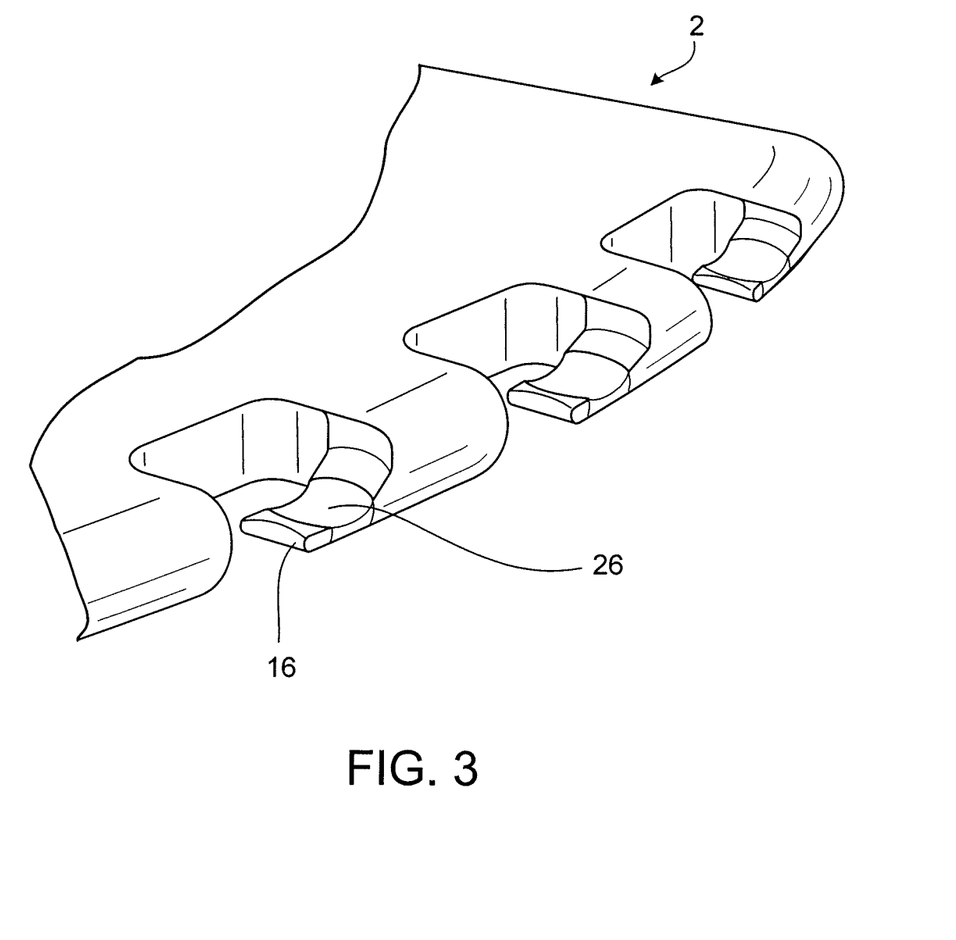
FIG. 3 is a perspective view of a molded dialysis solution bag hook of the portable cart of FIG. 1.

The top shelf 2 may additionally comprise one or more tapered hooks 16 for loading and hanging dialysis solution bags therefrom. Further referring to FIG. 3, the hooks 16 are formed by a cut-out of the top shelf 2, and have a tapered portion 26 that facilitates hanging at least one solution bag 24 therefrom. The at least one hook 16 is of a width and material strength sufficient to support a solution bag 24 that holds between approximately 1 liter and 6 liters of solution. In certain embodiments, the length of the hook is approximately between 1 and 2 inches. In one aspect, the length of the hook is approximately 1.5 inches. In other embodiments, the width of the hook is approximately between 0.5 and 1.5 inches. In one aspect, the width of the hook is approximately 1 inch. In certain embodiments, the depth of the hook is approximately between 0.2 and 1 inch. In one aspect, the depth of the hook is approximately 0.5 inches. The top shelf 2 may further include a handle 14 cut out for the user to easily grasp and move the cart.

Figure 9:
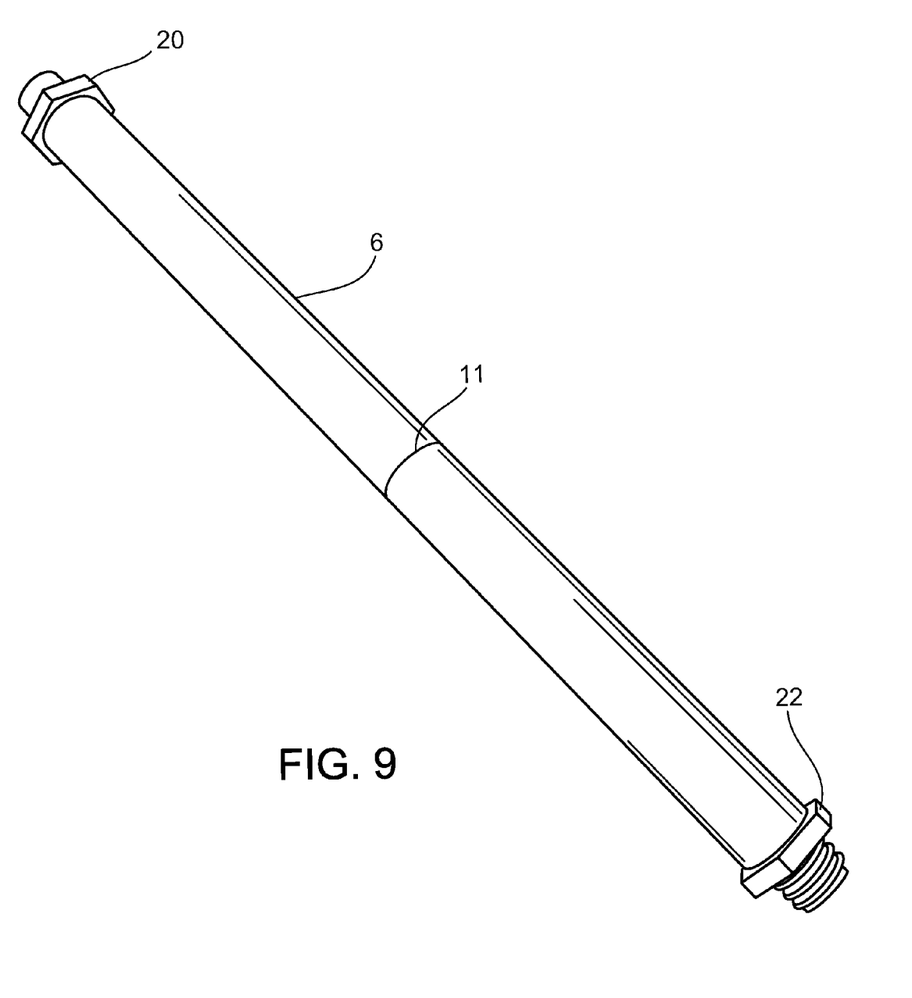
FIG. 9 is a perspective view of an adjustable connecting member that can be used in the portable cart of FIG. 1.

Referring to FIG. 2, at least four connecting members 6 connect to the bottom surface of the top shelf 2 and to the top surface of the bottom shelf 8. When the cart 10 is assembled, the connecting members 6 are approximately parallel to each other and perpendicular to the top and bottom shelves 2, 8, and the top shelf 2 is approximately parallel to the bottom shelf 8. The connecting members 6 may be adjustable in length so that the height of the top shelf 2 may be raised or lowered to optimize treatment for the patient. For example, a cart may come with several sets of connecting members 6, each set of a different length that may be used depending upon the height of the patient's bed. In other embodiments, the connecting members 6 themselves may be adjustable. Referring to FIG. 9, for example, the connecting members 6 may comprise two separate pieces meeting at interface 11, one that slides into the other, and can lock to each other at various different lengths. One of ordinary skill in the art can readily apply various extension and retraction technologies to the connecting members to achieve adjustable components.

Figure 4:
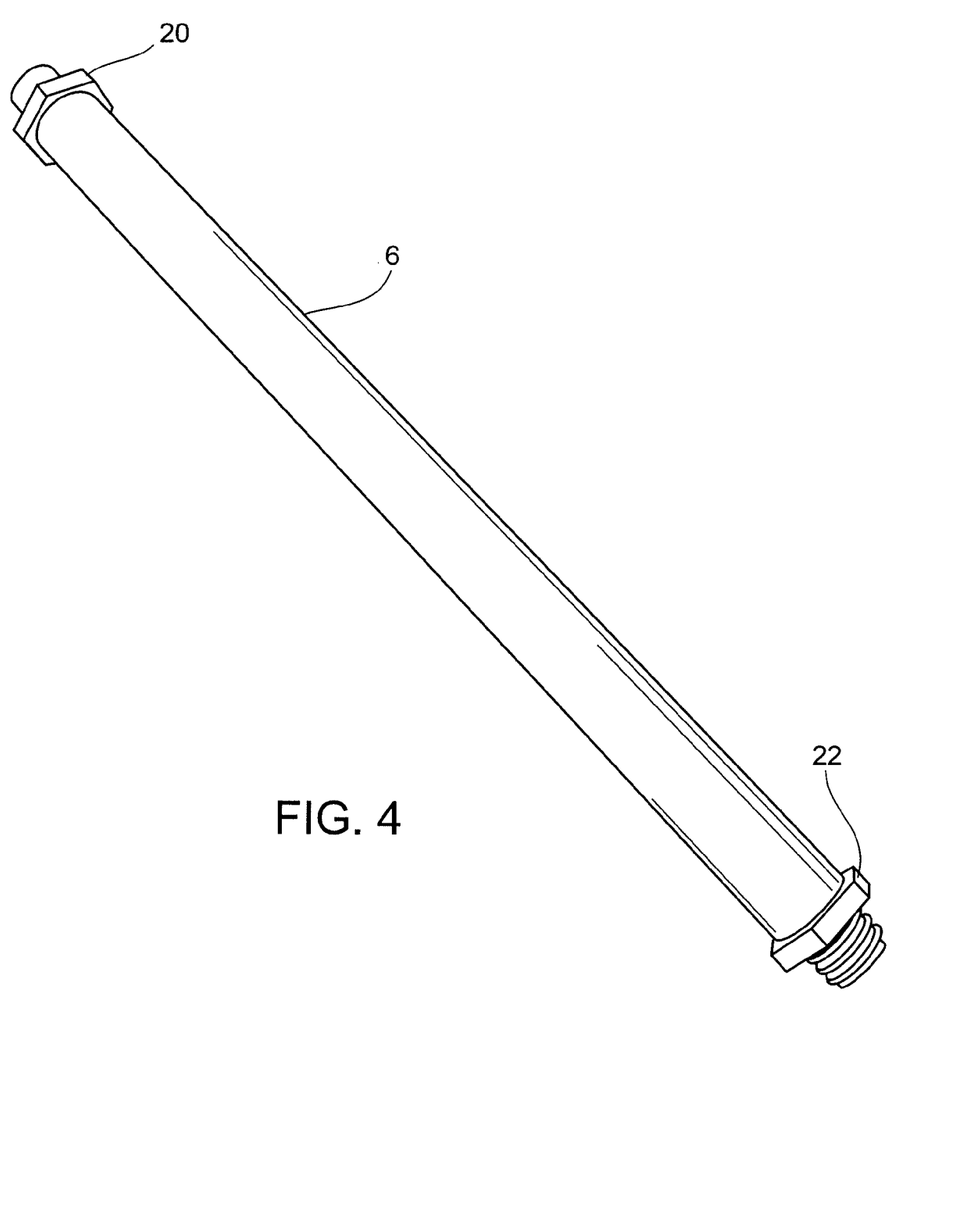
FIG. 4 is a perspective view of a connecting member of the portable cart of FIG. 1.
Figure 5:
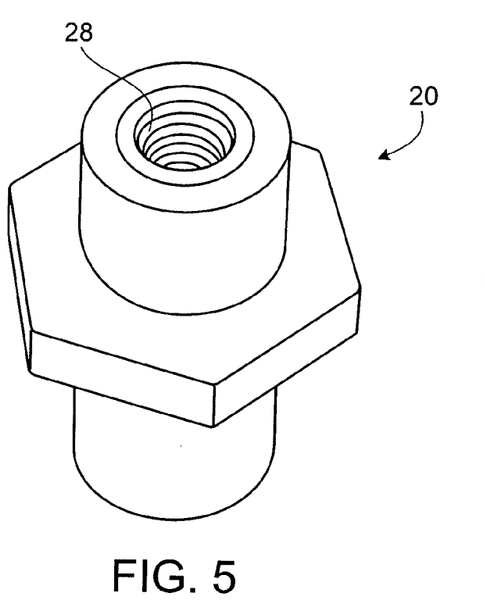
FIG. 5 is a perspective view of a tube end of the connecting member of FIG. 4.
Figure 6:
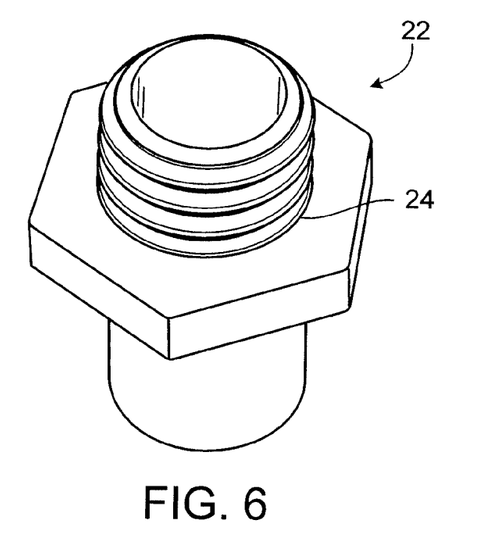
FIG. 6 is a perspective view of another tube end of the connecting member of FIG. 4.
Figure 7:
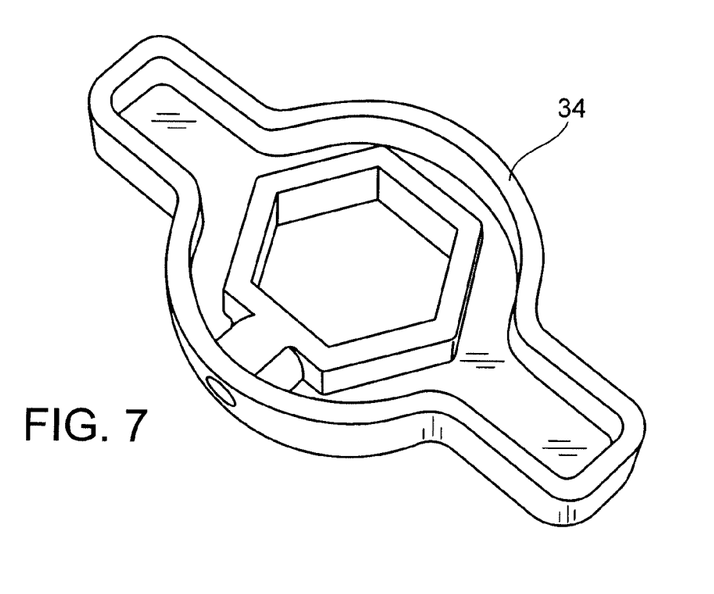
FIG. 7 is a perspective view of a washer or caster nut that is used between a caster and a bottom shelf of the portable cart of FIG. 1.
Figure 8:
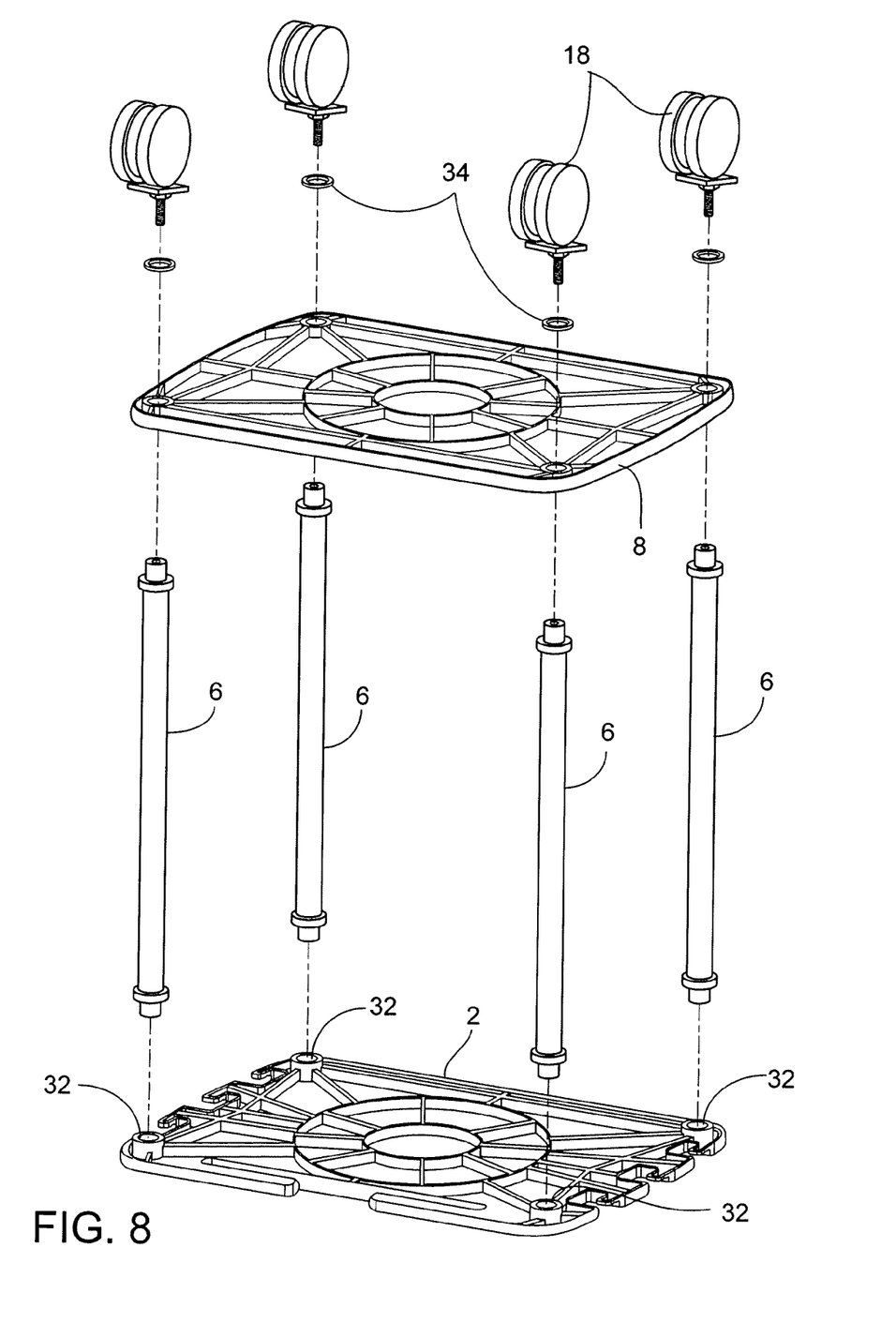
FIG. 8 is an exploded view of the portable cart of FIG. 1.

Referring to FIGS. 4, 5, and 6, the connecting member 6 has two ends 20, 22. The two ends 20, 22 press fit, or are otherwise secured, into the connecting member 6. In the embodiment shown, the two ends 20, 22 are different. However, for manufacturing and user simplicity, the two ends 20, 22 can also be the same as one another. In the embodiment shown, however, the end 20 is designed to attach to the bottom surface of the top shelf 2, and the end 22 is designed to attach to the top surface of the bottom shelf 8. To facilitate the connections to the shelves, end 20 is molded with threading on the inside 28, and end 22 is molded to have threading on the outside 24. As shown in FIG. 7, the bottom shelf 8 has recessed portions 30 on the top surface of the shelf 8 into which end 22 is designed to thread. Similarly and as shown in FIG. 8, the top shelf 2 has recessed portions 32 on the bottom surface of the shelf 2 into which end 20 is designed to thread. The connecting members 6 are therefore press fitted together and screwed into the shelves 2, 8 without necessitating any tools, complex mechanisms, or excessive physical strength.

As seen in FIGS. 2 and 8, casters 18 are attached to the bottom surface of the bottom shelf 8. These casters 18 allow the cart 10 to roll across a floor surface and may further include a braking mechanism (not shown) to lock the casters 18 into place and prevent the cart from rolling. Different size wheels and/or casters 18 can be used to facilitate or inhibit the portability of the cart. For example, larger wheels or casters may be used for deeper threaded carpet and smaller wheels or casters for hardwood, tile or marble surfaces. Washers or caster nuts 34 may be used between the bottom surface of the bottom shelf 8 and the casters 18 to facilitate caster 18 (and cart 10) movement.

As discussed above, the various embodiments of the present application are designed to hold and support a PD cycler and solution bags. PD cyclers generally weigh between approximately 20 and 50 pounds. For example, the Liberty® cycler weighs approximately 32 pounds. As different size or weight solution bags are used (described above), as solution bags fill and empty throughout a treatment cycle, and as bags are loaded or unloaded from the cart, the cart remains properly weighted so that the cart does not become unstable or tip.

The various components of the cart, including but not limited to, the top shelf 2, bottom shelf 8, connecting members 6, hooks 16, handle 14, connecting member ends 20, 22, and washer or caster nuts 34 may all be made via injection molding using plastic and a foaming agent. In some embodiments, the plastic is a thermoplastic. In other embodiments, plastics that may be used include but are not limited to: polyphenylene oxide, polystyrene, polycarbonate, acrylonitrile butadiene styrene, and/or equivalents thereof. The plastic is self-extinguishing, or "V0 Rated" plastic. In one aspect, the plastic used is Noyrl plastic (e.g., 215X). Foaming Agents, also known as Blowing or Nucleating Agents, eliminate sink marks, reduce density, shorten cycle time and reduce total production costs. In extrusion and injection molding, foaming agents save on material weight and lower total cost. They also improve extrusion rates by increasing the volume that can be processed per extruder in a given period of time, and endothermic foaming agents absorb heat and improve injection molding cycle time. Foaming agents that may be used comprise a concentration suitable for the plastics resins mentioned above. In one aspect, the foaming agent is Cel-Span® 899PS by Phoenix Plastic. In certain embodiments, the foaming agent is between approximately 1-10% of the total material mix. In one aspect, the foaming agent is between approximately 2-2.5% of the additive-plastic material mix. This method of manufacture allows the assembled cart to be both sturdy and lightweight. In various embodiments, the assembled cart (or all of the pieces of the disassembled cart taken together) weighs less than 20 pounds.

This method further allows the mold cavities to be filled with foaming plastic without the necessary high pressures of injection molding with other materials. The lower pressures of this method of manufacture also eliminate hardened steel molds or other high pressure molds (which are more costly) necessary for high pressure injection molding materials. Lower tooling costs and shorter run times are just a few examples of cost savings associated with this method. Color in the plastic and foaming agent eliminates the need for painting the cart, thereby increasing the sterility and cost savings of the cart.

The foregoing description is to be understood as being representative only and is not intended to be limiting. Alternative systems and techniques for making and using the compositions and devices of the invention and for practicing the inventive methods will be apparent to one of ordinary skill in the art and are intended to be included with the accompanied claims.

What is claimed is:

1. A cart for facilitating peritoneal dialysis treatment, the cart comprising:
   a top shelf component comprising
      a top surface to support a peritoneal dialysis machine,
      a plurality of cut-outs that extend inwardly from a side edge of the top shelf component, each cut-out being defined by first and second surfaces that extend inwardly from the side edge of the top shelf component and a third surface that joins the first surface to the second surface,
      a hook extending from the first surface in a direction substantially perpendicular to the first surface within each of the cut-outs, each hook having a top surface that extends substantially parallel to the top surface of the top shelf component and that defines an upwardly facing concave depression to receive hanging bags of solution, and
      a handle;
   a bottom shelf component substantially parallel to the top shelf component, and
   at least four connecting members, wherein each of the connecting members has one end connected to the top shelf component and an opposite end connected to the bottom shelf component, and wherein the connecting members are substantially parallel to one another, and wherein the top shelf component, the bottom shelf component, and the at least four connecting members comprise a plastic and a foaming agent additive.

2. The cart of claim 1, further comprising casters connected to the bottom shelf component.

3. The cart of claim 2, further comprising a locking or breaking mechanism configured to inhibit rotations of at least one of the casters.

4. The cart of claim 1, wherein the cart weighs less than 20 pounds.

5. The cart of claim 1, wherein the length of the connecting members is adjustable.

6. The cart of claim 1, wherein the plastic comprises polyphenylene oxide.

7. The cart of claim 1, wherein the plastic comprises one or more members selected from the group consisting of polyphenylene oxide, polystyrene, polycarbonate, and, acrylonitrile butadiene styrene.

8. The cart of claim 1, wherein the foaming agent additive comprises an approximately 20% active endothermic foaming agent concentrate.

9. The cart of claim 1, wherein the connecting members are releasably connected to the top shelf and the bottom shelf.

10. The cart of claim 1, wherein the cart is constructed to be assembled and disassembled without the use of tools.

11. A peritoneal dialysis system, comprising:
   a peritoneal dialysis machine; and
   a cart constructed to support the peritoneal dialysis machine, the cart comprising
      a top shelf component comprising
         a top surface to support,
         a plurality of cut-outs that extend inwardly from a side edge of the top shelf component, each cut-out being defined by first and second surfaces that extend inwardly from the side edge of the top shelf component and a third surface that joins the first surface to the second surface, and
         a hook extending from the first surface in a direction substantially perpendicular to the first surface within each of the cut-outs, each hook having a top surface that extends substantially parallel to the top surface of the top shelf component and that defines an upwardly facing concave depression configured to receive hanging bags of solution,
      a bottom shelf component substantially parallel to the top shelf component; and
      a plurality of connecting members that extend between the top shelf component and the bottom shelf component,
   wherein the top shelf component, the bottom shelf component, and the connecting members comprise a plastic and a foaming agent additive.

12. The cart for facilitating peritoneal dialysis treatment of claim 1, wherein the top surface of the top shelf component defines a plurality of circular indentations arranged in a rectangular configuration, wherein each of the circular indentations is located in a region of the top shelf component that is centrally spaced from a peripheral edge region of the top shelf component in which each of the connecting members connects to the top shelf component.

13. The peritoneal dialysis system of claim 11, wherein the top surface of the top shelf component defines a plurality of circular indentations arranged in a rectangular configuration, wherein each of the circular indentations is located in a region of the top shelf component that is centrally spaced from a peripheral edge region of the top shelf component in which each of the connecting members connects to the top shelf component.

14. A peritoneal dialysis system, comprising:
   a peritoneal dialysis machine; and
   a cart constructed to support the peritoneal dialysis machine, the cart comprising
      a top shelf component comprising
         a top surface defining a plurality of circular indentations arranged in a rectangular configuration, and
         at least one hook having a top surface defining a depression configured to receive hanging bags of solution,
      a bottom shelf component substantially parallel to the top shelf component; and
      a plurality of connecting members that extend between the top shelf component and the bottom shelf component, each of the connecting members being connected to a peripheral edge region of the top shelf component,
   wherein each of the circular indentations defined by the top surface of the top shelf component is located in a region of the top shelf component that is centrally spaced from the peripheral edge region of the top shelf component, and wherein the top shelf component, the bottom shelf component, and the connecting members comprise a plastic and a foaming agent additive.

15. The peritoneal dialysis system of claim 14, wherein the indentations are configured to align with and receive protrusions extending from a bottom surface of the peritoneal dialysis machine when the peritoneal dialysis machine is positioned atop the cart.

16. The peritoneal dialysis system of claim 14, wherein the top surface of the top shelf component defines four circular indentations arranged in corners of a rectangle formed by the rectangular configuration, and the top surface of the top shelf component defines another circular indentation positioned in a center region of the rectangle.

17. The peritoneal dialysis system of claim 14, wherein the circular indentations are blind holes.

18. A cart for facilitating peritoneal dialysis treatment, in combination with a peritoneal dialysis machine, the cart comprising:
  a top shelf component comprising
    a top surface defining a plurality of circular indentations arranged in a rectangular configuration, and
    at least one hook having a top surface defining a depression configured to receive hanging bags of solution,
  a bottom shelf component substantially parallel to the top shelf component; and
  a plurality of connecting members that extend between the top shelf component and the bottom shelf component, each of the connecting members being connected to a peripheral edge region of the top shelf component,
  wherein each of the circular indentations defined by the top surface of the top shelf component is located in a region of the top shelf component that is centrally spaced from the peripheral edge region of the top shelf component, wherein the circular indentations are configured to align with and receive protrusions extending from a bottom surface of the peritoneal dialysis machine when the peritoneal dialysis machine is positioned atop the cart, and wherein the top shelf component, the bottom shelf component, and the connecting members comprise a plastic and a foaming agent additive.

19. The cart of claim 18, wherein the top surface of the top shelf component defines four circular indentations arranged in corners of a rectangle formed by the rectangular configuration, and the top surface of the top shelf component defines another circular indentation positioned in a center region of the rectangle.

* * * * *

UNITED STATES PATENT AND TRADEMARK OFFICE
CERTIFICATE OF CORRECTION

PATENT NO. : 8,720,913 B2  
APPLICATION NO. : 12/850237  
DATED : May 13, 2014  
INVENTOR(S) : Joseph Michael Fallon et al.

Page 1 of 1

It is certified that error appears in the above-identified patent and that said Letters Patent is hereby corrected as shown below:

On the Title Page

On page 4, column 2, after "Other Publications", delete "Gam Bro" and insert --Gambro--.

In The Claims

On column 5, line 67 (Claim 11, line 67), delete "support," and insert --support the peritoneal dialysis machine,--.

Signed and Sealed this  
Seventh Day of April, 2015

Michelle K. Lee  
*Director of the United States Patent and Trademark Office*